United States Patent [19]

Williams

[11] 4,317,447
[45] Mar. 2, 1982

[54] DRUG DELIVERY SYSTEM

[75] Inventor: Bernard L. Williams, Martinsville, N.J.

[73] Assignee: Ortho Pharmaceutical Corporation, Raritan, N.J.

[21] Appl. No.: 58,881

[22] Filed: Jul. 19, 1979

[51] Int. Cl.³ .................. A61M 7/00; A61F 13/20
[52] U.S. Cl. .................................. 128/260; 128/270
[58] Field of Search ............ 128/260, 261, 263, 270, 128/285

[56] References Cited

U.S. PATENT DOCUMENTS

| | | | |
|---|---|---|---|
| 2,734,505 | 2/1956 | Parish | 128/285 |
| 3,369,544 | 2/1968 | Crockford | 128/285 |
| 3,390,671 | 7/1968 | Hildebrand | 128/263 |
| 3,639,562 | 2/1972 | Gordon et al. | 128/270 |
| 3,756,238 | 9/1973 | Hanke | 128/270 |
| 3,948,263 | 4/1976 | Drake, Jr. et al. | 128/260 |
| 4,043,339 | 8/1977 | Roseman | 128/260 |
| 4,179,497 | 12/1979 | Cohen et al. | 128/260 |
| 4,186,742 | 2/1980 | Donald | 128/270 |
| 4,237,888 | 12/1980 | Roseman et al. | 128/270 |

Primary Examiner—C. Fred Rosenbaum
Attorney, Agent, or Firm—Benjamin F. Lambert

[57] ABSTRACT

A drug delivery system comprising a soluble medicated polymer in the shape of a cartridge or capsule is described. The capsule is applied over a carrier and the drug is released upon disintegration of the cartridge after insertion into the vagina.

17 Claims, 3 Drawing Figures

DRUG DELIVERY SYSTEM

The present invention relates to a method of delivering therapeutic drugs to the vagina. Generally speaking, most vaginal therapeutic drugs are delivered by means of creams, foams, suppositories, gels or tablets. Although all of these methods are adequate for the purpose, there are disadvantages associated with some of the methods such as the need for an applicator, the need to clean the applicator for reuse, leakage resulting in drug loss and retarded drug availability due to the type of formulation used.

The present invention relates to an improved method of delivering drugs to the vagina wherein a water-soluble polymeric material, shaped in the form of a cartridge or sheath, is impregnated with a medicament and inserted into the vagina. The medicament is released as the polymer disintegrates in the vaginal fluids.

In a preferred embodiment of the invention, a tampon is inserted into the cartridge prior to insertion into the vagina. As the tampon expands to fill the vaginal cavity, it brings the polymer/drug system into close contact with the vaginal wall surface. The tampon serves to maintain the surface area and to absorb discharges which may result from certain infections.

Although a tampon is the preferred carrier, other carriers may be employed such as sponges or molded foam inserts. Thus, in addition to convenience of application, maximal utilization of the drug is achieved.

In the drawings

Figure 1:
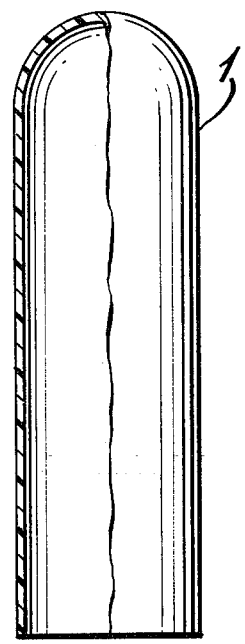
FIG. 1 shows a top view of the polymeric sheath.
Figure 2:
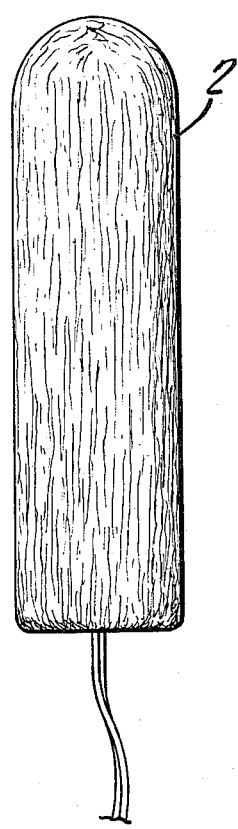
FIG. 2 shows a top view of a tampon like device prior to insertion into the sheath.
Figure 3:
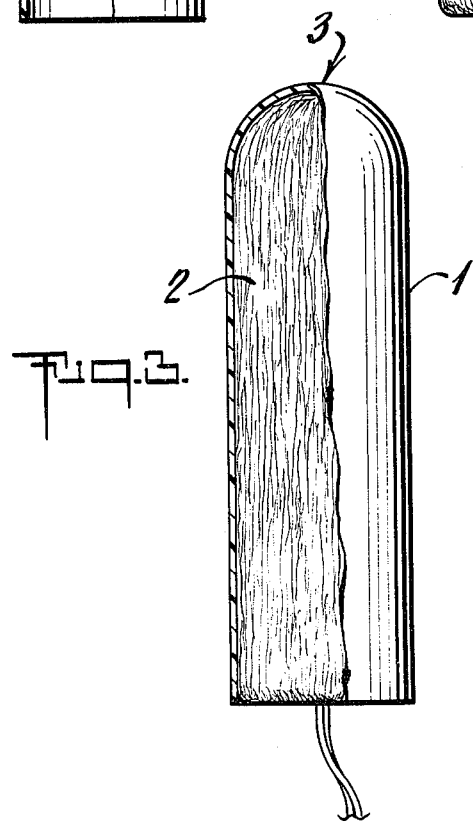
FIG. 3 shows a complete perspective view of the tampon encased in the polymeric sheath.

In FIG. 1, the polymeric sheath 1 is shown as a cylinder open at one end and having a spheroidal tip at its opposite end. A tampon 2 shaped to conform to the contour of the sheath is shown in FIG. 2. In FIG. 3, the tampon 2 is shown encased in the polymeric sheath 1. As shown in FIG. 1, the sheath preferably has a continuous outer wall without borings or openings. In this case, the passage of moisture and body secretions towards the tampon occurs when the sheath 1 dissolves in the vaginal fluids. The rounded end of the sheath 1 makes its introduction relatively easy. Although a cylindrical shape is preferred for the device, and suitable shape which can be introduced into the vaginal cavity may be employed.

The art of coating tampons with permeable or soluble films and melt or soluble suppository formulations containing medicaments has been described in the literature. U.S. Pat. No. 3,756,238 describes a self-lubricating compound suitable for hygenic medical applications, such as for coating tampons and as suppository structures. The compound contains a thermoplastic film-forming water-soluble polymer and the lubricant has the ability to form a homogeneous blend or a solution with the polymer at elevated temperatures. The lubricant on the surface of the polymer provides an initial spontaneous lubricity to the non-eroded surface of the compound to ease insertion immediately as well as adding lubricity to newly exposed surface as the compound is eroded away by a dissolving action. The controlled erosion continually releases fresh medicament.

U.S. Pat. No. 3,805,785 describes a feminine pad for internal use which is provided with a coating or sheath made up of a jelly-like material. The jelly-like coating, however, serves no other purpose then to make application of the pad easier due to the fact that the jelly-like substance melts or dissolves with body heat.

Coatings such as those described in the literature are generally applied by dipping, spraying or the like. The present invention relates to an improved delivery system wherein the polymer is first impregnated with the medicament and then shaped into a cartridge or capsule which will fit over a carrier such as a tampon. Any size carrier can be employed since the polymer can be shaped to fit the carrier. The polymer may comprise any of the polymers which are soluble in body fluids such as, for example, modified cellulose, polyvinyl alcohol, polyvinylpyrrolidone, polyacrylamide, an ethyleneoxide polymer and the like. Preferably the solubility characteristics of the polymer are chosen so that the entire mass is totally dissolved in the body cavity fluids within a period of about twenty-four hours so as to give sustained, prolonged release of the medicament. The preferred polymer is a hydroxypropyl cellulose or a hydroxypropylmethyl cellulose having a molecular weight of from about 60,000 to about 1,000,000. Typically empoyable in the present invention are cellulose ethers having a high degree of ideal propyl substitution at the hydroxyl groups. From 80 to 100 percent propyl substitution is suitable.

The medicated polymer is prepared by dry blending the medicament with the polymer, preferably in powdered form, until a uniform mixture is formed. The mixture is then thermally melted and extruded as rods which, after cooling, are cut into pellets. The pellets are then melted and the polymer/drug mixture is injection or compression molded, thermally extruded into cavities of the desired shape, or the extrudate is compression molded. The preferred shape is a capsule having one end open which can be applied over a tampon. A plasticizer such as glycerine, propylene glycol or polypropylene glycol may be added to the mixture prior to molding in order to prevent cracking. The plasticizer also aids in releasing the capsule from the mold.

The concentration of the medicament in the capsule or cartridge may vary from small amounts up to about 50% by weight of the molded capsule. The actual amount employed will depend upon the particular polymer/medicament selected and the condition being treated. Dosages, of course, should be controlled in accordance with standard practices. The only criterion is that an effective amount of the medicament be contained in the capsule. Substances which are particularly suitable for use in the present invention include bactericides, fungicides, antibiotics and the like which may be selectively chosen for use in controlling bacteria, protozoa and fungi including trichomonous vaginalis, candida albicans and the like. Compounds which can be employed include steroidal medicaments and estrogenic compounds such as cortesone, estradiol, prednisolone, progesterone, pregnenolone and pharmaceutically acceptable salts thereof. Other compounds which can be employed include miconazole nitrate, dienestrol, sulfathiazole, sulfacetamide and sulfabenzamide. Spermicidal compounds which are compatible with the polymer may also be employed. Typically acceptable spermicides are polyoxyethylenated-p-menthanylphenol and the nonionic surfactants such as ethoxylated phenoxyethanols. The later materials are well known in the art and are represented by p-diisobutylphenoxypolyethoxy ethanol, nonylphenoxypoly(ethoxy)$_n$, ethanol (where n is an integer from 7 to 21), ricinoleic acid and mercurial salts such as phenylmercuric acetate. The preferred spermicides are the nonylphenoxypoly(ethyoxy)$_n$ ethanols such as nonoxynol-9.

In a preferred embodiment of the invention, a blend of the following proportions is made, extruded, and chopped into pellets: Klucel EF, hydroxypropyl cellulose (86%), miconazole nitrate (10%), Carbowax 400 (3%), and Anti-Foam A, a food grade silicone product, (1%). These pellets are then extruded over a temperature range of 295° to 345° F. directly into an appropriately shaped compression mold and molded under high compression force into a capsule or cartridge form. This molded unit is then placed over a tampon and the encapsulated tampon is inserted inside a conventional applicator such as those used for menstrual purposes. The inserter serves to facilitate placement of the medicated cartridge. During residence in the vagina, the available moisture from the vaginal wall and from the cervical glands slowly dissolves the polymeric cartridge, thus releasing the medicament over an extended period of time. The hydroxypropyl cellulose polymer, upon hydration, converts to a high viscosity gel which provides a soothing effect on the vaginal wall. In addition, the gel insures retention of the medication over the entire surface of the tampon. As additional moisture forms and a thinning of the gel occurs, the tampon is now free to absorb these excess fluids as well as purulent discharges arising from the infection. After a period of time the tampon is removed and discarded. The frequency of application will depend upon the physician's recommendations.

The following examples are given by way of illustrating the invention but are not intended to limit the invention.

| Example 1 | hydroxypropyl cellulose | 900 mg |
| --- | --- | --- |
| | miconazole nitrate | 100 mg |
| Example 2 | hydroxypropyl cellulose | 995.5 mg |
| | dienestrol | 0.5 mg |
| Example 3 | hydroxypropyl cellulose | 1000 mg |
| | sulfathiazole | 172.5 mg |
| | sulfacetamide | 143.5 mg |
| | sulfabenzamide | 184.0 mg |

By means of the present invention it is possible to incorporate effective quantities of a medicament as an integral part of a smooth surfaced capsule. Precision dosage tolerances can be readily achieved while a fast and simple mechanical operation for applying the capsule to the tampon is inherent in the concept. Since the tampon and capsule are manufactured separately, the union of the two in a totally dry state helps to maintain the integrity of the tampon. The dosage form can withstand a wide range of temperature and humidity.

I claim:

1. A device for delivering a medicament to the vaginal cavity consisting of a molded polymeric sheath having at least one open end, said sheath consisting of an intimate mixture of a polymeric material and a medicament and being dissolvable in body fluids, said device being capable of slowly releasing said medicament while dissolving in said body fluids.

2. The device of claim 1 wherein the polymeric material is a hydroxypropyl cellulose.

3. The device of claim 1 wherein the medicament is a spermicide, ovacide, antimicrobial, prostaglandin, steriodal or non-steroidal antifertility agent.

4. The device of claim 3 wherein the medicament is a spermicide.

5. The device of claim 4 wherein the spermicide is nonoxynol-9.

6. The device of claim 3 wherein the medicament is an antimicrobial agent.

7. The device of claim 6 wherein the antimicrobial agent is miconazole nitrate.

8. The device of claim 3 wherein the medicament is present in an amount ranging from about 0.5 to about 35 percent by weight.

9. A device for delivering a medicament to the vaginal cavity comprising a molded polymeric sheath having an open end and a closed end and a catamenial device adapted for insertion into the vaginal cavity, said sheath comprising an intimate mixture of a polymeric material and a medicament, and being inserted over said catamenial device, dissolvable in body fluids and capable of slowly releasing said medicament while dissolving in said body fluids.

10. The device of claim 9 wherein the polymeric material is a hydroxypropyl cellulose.

11. The device of claim 9 wherein the medicament is a spermicide, ovacide, antimicrobial, prostaglandin, steroidal or non-steroidal antifertility agent.

12. The device of claim 11 wherein the medicament is a spermicide.

13. The device of claim 12 wherein the spermicide is nonoxynol-9.

14. The device of claim 11 wherein the medicament is an antimicrobial agent.

15. The device of claim 14 wherein the antimicrobial agent is miconazole nitrate.

16. The device of claim 9 wherein the catamenial device is a tampon.

17. The device of claim 9 wherein the medicament is present in an amount ranging from about 0.5 to about 35 percent by weight.

* * * * *